United States Patent [19]
McLean

[11] Patent Number: 5,935,610
[45] Date of Patent: *Aug. 10, 1999

[54] COMPOSITION HAVING BUFFERING PROPERTIES

[76] Inventor: Linsey McLean, G-4267 S. State Rd., Davison, Mich. 48423

[*] Notice: This patent issued on a continued prosecution application filed under 37 CFR 1.53(d), and is subject to the twenty year patent term provisions of 35 U.S.C. 154(a)(2).

[21] Appl. No.: 08/612,022

[22] Filed: Mar. 5, 1996

Related U.S. Application Data

[63] Continuation-in-part of application No. 08/112,768, Aug. 26, 1993, Pat. No. 5,496,567.

[51] Int. Cl.$^6$ .......................... A61K 33/32; A61K 33/10; A61K 33/08
[52] U.S. Cl. ......................... 424/643; 424/686; 424/688
[58] Field of Search ...................... 424/687, 692, 424/643, 686, 688; 514/251, 345, 52, 925, 926, 927

[56] References Cited

U.S. PATENT DOCUMENTS

| | | |
|---|---|---|
| 3,092,548 | 6/1963 | Worton ................................... 424/687 |
| 3,215,601 | 11/1965 | Stolar . |
| 3,253,988 | 5/1966 | Scott . |
| 3,272,703 | 9/1966 | Rubino et al. . |
| 3,843,778 | 10/1974 | Diamond et al. . |
| 4,327,076 | 4/1982 | Puglia et al. . |
| 4,327,077 | 4/1982 | Puglia et al. . |
| 4,396,604 | 8/1983 | Mitra . |
| 4,446,135 | 5/1984 | Fountaine . |
| 4,486,412 | 12/1984 | Shah et al. . |
| 4,486,435 | 12/1984 | Schmidt et al. ......................... 424/252 |
| 4,533,543 | 8/1985 | Morris et al. . |
| 4,545,989 | 10/1985 | Becker et al. . |
| 4,581,381 | 4/1986 | Morris et al. . |
| 4,605,551 | 8/1986 | Buehler et al. . |
| 4,704,269 | 11/1987 | Korab . |
| 4,764,374 | 8/1988 | Grimberg . |
| 4,867,989 | 9/1989 | Silva et al. . |
| 4,888,185 | 12/1989 | Miller . |
| 4,937,076 | 6/1990 | Lapidus . |

OTHER PUBLICATIONS

Geoffrey Cowley, "Here's the Beef!", *Newsweek* Magazine, Feb. 5, 1996, pp. 54–55.

Earl Mindell's Vitamin Bible, (Warner Books), pp.31, 32, 169, 170 and 236, 1991.

Remington's Pharmaceutical Sciences, 16th edition, pp. 1555–1557, 1980.

*Primary Examiner*—Raymond Henley, III
*Attorney, Agent, or Firm*—Harness, Dickey & Pierce, P.L.C.

[57] ABSTRACT

A pharmaceutical composition having buffering properties comprises as its primary ingredients calcium carbonate ($CaCO_3$) and magnesium oxide (MgO; magnesia) that form the base for the compound. Potassium sorbate ($CH_3CH$:CHCH:CHCOOK) is provided as a preservative. Other ingredients include a tabletizing binder, vitamin complexes, minerals as antipathogens, and flavorings.

16 Claims, No Drawings

COMPOSITION HAVING BUFFERING PROPERTIES

CROSS REFERENCE TO RELATED APPLICATION

This application is a continuation-in-part of application Ser. No. 08/112,768, filed Aug. 26, 1993, now U.S. Pat. No. 5,496,567 which is hereby incorporated by reference.

Background of the Invention

I. Field of the Invention

The present invention relates to compositions of matter having buffering and nutritional properties. More particularly, the present invention relates to a composition that includes an antacid base comprising magnesium oxide as the primary active ingredient and calcium carbonate. The composition further includes one or more supplemental vitamins and/or one or more trace minerals, such as zinc oxide. The composition of the present invention has both buffering and nutritional properties. The composition is administered in a tablet or powder form.

II. Description of the Relevant Art

Magnesium, calcium, and phosphorous are macrominerals which are all necessary—in proper ratios—for proper functioning of living things. An overabundance of one or the other of the minerals is problematic. Such a situation is present environmentally where phosphates are highly prevalent and are not only in food and soft drinks, but are also in washing materials and fertilizers. Phosphates have, in fact, become overly abundant when compared with the other two macrominerals. This is apparent environmentally in the case of excessive algae growth in bodies of water (where algae thrives on phosphates, just as growing grass does, hence the reason for its inclusion in fertilizers).

Growth in the corn plant is an example of how the imbalance of macrominerals was done intentionally, and how this imbalance has entered the food chain. At one time a relatively low-dose formulation of phosphate was used as a fertilizer for growing crops, such as corn. The stalk of the corn depends upon calcium and magnesium for proper growth, while the seedhead (containing the highest amount of protein, and, of course, protein contains phosphate [in the DNA]) depends upon magnesium. About the time of the oil embargoes of the 1970's, however, it was discovered that a concentrated form of phosphate, a "superphosphate", could be used to accelerate the growth of the seedhead. However, the stalk remained stunted.

Between our fast food diets and the rampant use of phosphates in fertilizers, living organisms have excess amounts of phosphates with inadequate amounts of calcium and magnesium. In fact, the total amount of magnesium in today's diet represents only about 25% of the magnesium in diets of persons of two generations ago. This imbalance presents a variety of problems. Phosphates, which are acidic, cause increased excitability in muscle tissue, and is thought to accordingly be a basis for problems in children such as attention deficit disorder and ADHT and the increased prevalence of ulcers in adults. (In fact, the prevalence of ulcers in grazing animals and race horses [90% of thoroughbreds are so afflicted] where "stress" is not a factor can be largely attributed to the increased amount of phosphate in the grains these animals eat. At one time such afflictions were simply unknown.) The amount of acidity in the background environment has been increased by acid rain.

This high-acid background coupled with modern lifestyles poses grave consequences to living systems. Life in modern times is, by definition, life in stressful times. The well-being of the individual is clearly compromised by the fast-paced, high-stress styles of life that most Westerners have come to expect as being normal and acceptable.

While many parts of the human body suffer from such a way of life, the stomach and the duodenum represent areas of the body that react most immediately and most vividly to increased stress on the individual.

Two undesirable situations result from stress. First, the body tends to absorb and metabolize important nutrients, particularly the B complex vitamins (the most important of which are vitamins $B_1$, $B_2$, $B_6$ and $B_{12}$), at a particularly fast rate. Also metabolized at an accelerated rate are metal elements including calcium, magnesium and zinc.

The second situation relates to the physical destruction of body tissue. In the healthy stomach, gastric mucus and epithelial barrier protect the stomach from "digesting itself". This is critical in that pure gastric juice is capable of digesting all living tissues. Pathogenically, severe and even mild stress works to compromise these lines of defense by causing an alteration in the permeability of the epithelial barrier, thereby allowing back diffusion of hydrochloric acid and contributing to the destruction of underlying tissue. If the body is unable to buffer the stomach acid, ulcers and nutritional deficiencies result, as well as bowel and colon problems. Furthermore, histamine is liberated and plays a role in the stimulation of additional acid and pepsin secretion. The mucosa is damaged as a result and erosions and ulcers may be formed. Plasma protein is lost at this stage.

In responding to the former situation, an increased uptake of selected vitamins and metals by the affected individual works to offset the loss due to stress. Regarding the latter situation, the primary objective in the treatment of erosions and ulcers is to inhibit (or buffer) the acid secretions. Such inhibition results in both relieving symptoms and encouraging healing of the affected region.

Humans have responded to the increased presence of acid in the system by ingesting an ever-increasing number of antacids. Antacids are useful for neutralizing the acid gastric contents by maintaining an elevated pH level such that pepsin is not activated. The buffering feature of antacids is generally provided by a weak base that becomes a buffer on the addition of acid.

Sodium bicarbonate was once the antacid of choice, but its popularity has fallen in light of the excessive amount of sodium in the diet. An alternate antacid uses aluminum, typically in the form of aluminum hydroxide gel ($Al_2O_3 \cdot xH_2O$). However, aluminum has been related to Alzheimer's disease on the theory that because aluminum is a neurotoxin, it can induce neurofibrillary changes in the brain. This is the result of aluminum toxicity. While it is not clear whether or not the link between the disease and aluminum is absolute, this theory persists.

An antacid presently of choice uses as its principal ingredient magnesium hydroxide ($Mg(OH)_2$), which also finds use as a laxative in milk of magnesia (magnesia magma) in a water suspension. However, this compound has been found to be too aggressive, effectively attempting to buffer when excess acidity did not even exist. This leads to a state of over-alkalinization, thus causing acid rebound where the body is trying to maintain a state of pH balance.

There are known some antacids that do not contain aluminum, but use other undesirable components. For example, some popular antacids contains "mineral oil and purified water". However, while mineral oil has for some time been used internally, it is now becoming clear that this is not desirable. Mineral oil taken internally has many negative effects. For example, mineral oil decreases absorption of vitamins A, D, E, and K, as well as calcium and phosphorous. Furthermore, mineral oil binds carotene from foods in the intestine as it passes. Mineral oil also passes into blood and into the lymph, and picks up additional fat soluble vitamins from body fluids and tissues and excretes these materials in the feces. In addition, mineral oil, which is often used as a laxative (thus the individual using the composition as an antacid will be receiving treatment with a laxative even if such treatment is unnecessary), is also under present suspicion as a contributor to cancer.

Buffering compositions not containing mineral oil are known. However, the compositions substitute mineral oil with other oils that are not desirable according to present knowledge. Specifically, all of the oils used in known compositions are either saturated or are polyunsaturated. Today it is understood that polyunsaturates contribute to cancer because of low-density lipoproteins ("LDL's") and because of the generation of free radicals. Polyunsaturates depress both the density of the LDL's while reducing the numbers of desirable high density lipoproteins ("HDL's").

Furthermore, only LDL elevation is associated with increased coronary risk, while HDL elevation correlates with decreased risk. Accordingly, HDL cholesterol has been referred to as "benevolent" cholesterol, and HDL elevation is increasingly being thought of as having protective effects.

Other approaches to resolving the problem of excess acidity in the human system include hydrogen-ion inhibitors which are directed to halting the production of stomach acid before it begins. The failing of these drugs is that without acid, food is not digested, and nutritional deficiency results.

Modern medicine has stepped back to reconsider the question of the calcium-magnesium-phosphate balance. The focus is now not on neutralizing acidity and reducing phosphates as much as it is by improving the overall balance of these macrominerals. In response to the increased acidity of the human diet caused by phosphates, attention was given to buffering the acid by the other two macrominerals. Accordingly, the amount of one of the macrominerals—calcium—has been intentionally increased. For example, milk has been supplemented with calcium.

However, the absence of magnesium from living systems has been largely ignored, in spite of the fact that about 98% of all biochemical reactions involve magnesium in either a primary, secondary, or tertiary way. Yet this third "leg" of the macromineral triangle remains wanting. Some more progressive nutritional experts have proposed increasing the presence of magnesium to a ratio of 4:1 with respect to calcium (1 part calcium to 0.25 parts magnesium). Yet this approach also fails to overcome the deficiencies of the modern diet.

Stressful conditions and environmental changes have lead to both excess acidity and nutrient (particularly vitamin) deprivation. There is presently no known pharmaceutical composition which attends to both of these difficulties as a single medication.

SUMMARY OF THE PRESENT INVENTION

The present invention provides a solution to the problems described above by offering the user both a means of reducing stomach acidity while at the same time providing a nutritional supplement for compromised individuals.

The composition of the present invention includes an antacid base. The base includes magnesium oxide as the principal component and calcium carbonate. Both magnesium oxide and calcium carbonate demonstrate buffering abilities, and both include ions which are generally inactive in a balanced pH system, but become active in an acidic system, thus providing a "buffering-on-demand" scenario. The composition may be administered in a tablet or powder form. A flow product (such as silicon dioxide) is used in forming the powder, while the flow product and a tabletizing binder ("sticker") are used to form the tablet.

Additional ingredients may be included. Such ingredients include a vitamin supplement comprising one or more selected vitamins. In addition, or in the alternative, one or more minerals (such as zinc oxide) may be added. The variety of vitamins and minerals provide nutritional support, healing, and recovery of the body.

Secondary ingredients may be added in the form of flavorings and sweeteners as needed.

One of the important ingredients of the present composition is the use of magnesium as a buffering agent. The main ingredient is magnesium oxide with calcium carbonate being present to prevent calcium deficiencies. (Magnesium oxide causes the body to excrete calcium.) The "balancing effect" caused by the provision of both magnesium oxide and calcium carbonate is particularly important in that magnesium is also perhaps the most deficient of minerals present in food in modern times. Also, magnesium is important in chemically polluted environments as in the present times. (The presence of calcium carbonate is also desirable in that calcium depletion is also caused by phosphorous which is present in today's food chain [largely because of today's fertilizers] to a toxic amount. Phosphorous causes the body to excrete calcium.)

The principal advantages of the present invention are that the user can obtain both relief from excess acidity and nutrition from the same medication without the fear of aluminum toxicity and without fear of incurring magnesium deficiency. These actions combined produce in the user a considerable sense of well-being for three reasons. First, the user's abdominal discomfort is diminished. Second, the effects of the selected vitamins (particularly B vitamins) and minerals (for example, zinc oxide) work to provide additional calm. Third, the healing effect of the vitamins and/or minerals improves the general health of the affected individual. The overall sense in the user is that stress is reduced emotionally as well as physically as a result of the effects of the present invention.

The present invention provides several advantages over known buffers. For example, by using magnesium oxide as a buffering agent (buffered by calcium), the composition of the present invention avoids the results normally seen with calcium carbonate used in many other buffers which creates a magnesium deficiency. In addition, by using magnesium oxide rather than magnesium hydroxide, an acid-rebound effect is avoided. This is an undesirable characteristic of known buffers which utilize so much buffering material that additional acid [the acid-rebound] is actually produced. Conversely, because the ingredients of the present invention are ordinarily insoluble in a balanced pH system, the composition only becomes activated in the present of treatment with acid. However, when exposed to acid, the buffering effect of the composition is initiated, responding in an "as needed" way such that the buffering activity of the composition increases as the amount of acid in the system increases. Without excess acid in the system, the composition passes through the body. Accordingly, the "on-demand" response of the present invention eliminates the known ill-effects produced by known compositions which tend to overtreat the acid problem.

Other objects and details of the present invention will become apparent from the following detailed description.

DETAILED DESCRIPTION OF THE PREFERRED EMBODIMENTS OF THE PRESENT INVENTION

The composition of the present invention includes as its basic components a base. The antacid base comprises two primary ingredients. These ingredients include magnesium oxide (magnesia) (MgO) and calcium carbonate ($CaCO_3$).

Magnesium oxide is slightly soluble in water and is soluble in acids. It is often used in pharmaceutical compositions. Magnesium helps to buffer acids at the cellular level.

Calcium carbonate, like magnesium oxide, is slightly soluble in water and is soluble in acids. It is provided as a component of the present invention to act as a neutralizing antacid.

According to the present invention, the two primary components of the base, calcium carbonate and magnesium oxide, function not only as buffering antacids but also as calcium and magnesium supplements. Both are essential substituents of living things. They are also known to relieve stress.

Additional ingredients of the composition of the present invention include a preservative such as potassium sorbate ($CH_3CH:CHCH:CHCOOK$) (other preservatives may be used), sweeteners and flavorings as needed.

Beyond the basic ingredients given above, a variety of additional ingredients may be included in the pharmaceutical composition according to the present invention. The additional ingredients include vitamin supplements and selected minerals.

The vitamin supplements are preferably those that are directed to the overall reduction of stress of the user, this in keeping with one of the main purposes of the invention. Accordingly, the vitamin B complex may be selected. This group preferably includes thiamine ($B_1$) (available as thiamine hydrochloride and thiamine mononitrate), riboflavin ($B_2$), different chemical forms of what is now considered to be $B_3$, different chemical forms of what is now considered to be $B_5$, pyridoxine HCl ($B_6$) and cyanocobalamin ($B_{12}$). These additives are used, when compatible with the other components, as microencapsulates. When used in this form, the microencapsulates are used to provide the composition in a tablet form. Additionally, the composition may be provided in a chewable form with, for example, a fruit flavor.

Other vitamins may be selected. For example, the antineuritic vitamin thiamine has particular application in reducing emotional hypersensitivity, muscular weakness and fatigue. Riboflavin is important in tissue respiration. Pyridoxine is essential for the dehydration and desulfydration of amino acids and for the normal metabolism of tryptophan. It also appears to be related to fat metabolism. Inadequate amounts of $B_{12}$ in humans results in deficiencies that include megaloblastic anemias and various neurologic disorders.

A variety of minerals may also be added. Zinc oxide may be used in lieu of or in addition to other minerals. Zinc enhances the body's immune system and this enhancement is believed to be beneficial against various pathogens including, it is further believed, *Helicobacter pylori* (previously called *Campylobacter pylori*), the bacteria commonly associated with gastritis and the formation of ulcers. In addition to assisting in the healing of the body, these minerals also provide supplementary amounts of calcium, magnesium and zinc, all necessary metals to maintain body health and metabolism. Furthermore, the minerals and vitamins promote easier and more complete absorption of nutrients by the body, while not changing the pH of the digestive tract which is a common reaction to inorganic salts.

Both vitamins and minerals are known to aid in the healing of the body.

The composition may be provided in a powder form for use with water or for use with milk to form a shake. In addition, the powder may be used with a "health" drink. In its powder form, a flow product (such as silicon dioxide) is provided.

The composition is alternatively provided as a tablet. In addition to the flow product, one or more tabletizing binders ("stickers") are used as needed to form the tablet. The flow product allows the powdered material to flow through the machinery, while the binder allows the material to assume and hold the tablet form upon compaction by the tablet-forming machine.

The ingredients that comprise the composition described above are used as needed in the present composition to provide a pharmaceutical composition in tablet or powder form having buffering properties while also having nutritional and healing properties.

General Formulation and Preparation of the Present Composition

The composition of the present invention is prepared by mixing the appropriate amount of individual materials together in dry form. If a powder product is preferred, the materials are mixed together and packaged. If a tablet product is preferred, the base materials are mixed together (also using a tabletizing binder) and are passed into a machine which forms the tablets.

Calcium carbonate and magnesium oxide are provided in a ratio of 5:4 by weight. However, while the major component by weight is calcium carbonate, elementally magnesium oxide outweighs calcium carbonate by about 2:1. (The 5:4 ratio of calcium carbonate to magnesium oxide actually results in 1.25 parts elemental calcium to 2.16 parts elemental magnesium.) This ratio gives the user a significantly higher amount of magnesium that is being taken up from the food supply.

Several optional ingredients may be added to the composition and, if added, are included at the creation of the second phase and prior to its being mixed. The optional ingredients include flavorings and sweeteners. Furthermore, and when compatible, B-complex vitamins, other vitamins and mineral supplements may be included as microencapsulates.

The recommended quantities of the components necessary for preparing a minimum workable amount of the present composition are as follows:

| | |
|---|---|
| Antacid base (calcium carbonate/magnesium oxide) | Provided in a 5:4 ratio |
| Tabletizer binder | Per recommendation of manufacturer |
| Flow product | Per recommendation of manufacturer |
| Preservative: | per recommendation of manufacturer |
| Flavorings | per recommendation |

| | |
|---|---|
| and Sweeteners: | of manufacturer |
| Vitamin Supplements: | 1–10% by weight |
| Mineral Supplements: | 1–10% by weight |

Many of these quantities may be varied based upon continued experimentation and improvements in concentrations of certain components.

I claim:

1. An orally administrable buffering composition for providing buffering in a living system, the composition comprising:
   a base, said base comprising
   (1) a selected amount of magnesium oxide; and
   (2) a selected amount of calcium carbonate, said calcium carbonate being provided in a lesser amount elementally than said magnesium oxide, said base being substantially insoluble in a neutral medium, said amount of calcium carbonate being sufficient to compensate for calcium deficiency effected by the metabolism of said magnesium oxide and said amount of magnesium oxide being sufficient to effect buffering,
   whereby the composition raises the pH of the living system to which it is administered.

2. The buffering composition of claim 1, further including a vitamin supplement.

3. The buffering composition of claim 2, wherein said vitamin supplement is in the amount of between 1 and 10 percent by weight.

4. The buffering composition of claim 3, wherein said vitamin supplement comprises B complex vitamins.

5. The buffering composition of claim 1, further including a mineral supplement.

6. The buffering composition of claim 5, wherein said mineral supplement is in the amount of between 1 and 10 percent by weight.

7. The buffering composition of claim 5, wherein said mineral supplement is zinc oxide.

8. The buffering composition of claim 1, further comprising a preservative.

9. The buffering composition of claim 1, further including a flavoring.

10. The buffering composition of claim 1, further including a flow product.

11. The buffering composition of claim 10, wherein said flow product is silicon dioxide.

12. The buffering composition of claim 1, further including a tabletizing binder.

13. An orally administrable buffering composition in tablet form for providing buffering in a living system comprising:
   a base, said base including a buffering ingredient that is substantially insoluble in a neutral medium, said base including magnesium oxide and calcium carbonate in a ratio sufficient to compensate for a calcium deficiency effected by the metabolism of said magnesium oxide, said ratio of magnesium oxide to calcium carbonate being in an amount elementally of approximately 2:1;
   a tabletizing binder;
   a vitamin in an amount of between 1 and 10 percent by weight; and
   a selected quantity of a mineral, said selected quantity being at least 1 percent by weight, whereby said vitamin is selected based upon its ability to reduce stress in the living system.

14. The orally administrable buffering composition of claim 13, further including a flow product.

15. The orally administrable buffering composition of claim 13, further including zinc oxide.

16. An orally administrable composition for providing buffering and nutritional supplement in a living system comprising:
   a base, said base consisting of:
   a quantity of magnesium oxide; and
   a quantity of calcium carbonate in an amount sufficient to compensate for calcium deficiency caused by said quantity of magnesium oxide, said base being substantially insoluble in a neutral medium, said quantity being a magnesium oxide-to-calcium carbonate ratio of about 2:1.

* * * * *